United States Patent [19]

Backhouse et al.

[11] Patent Number: 5,583,091
[45] Date of Patent: Dec. 10, 1996

[54] SYNERGISTIC FUNGICIDAL COMPOSITION AND USE

[75] Inventors: Bryan S. Backhouse, Leefdaal, Belgium; Malcolm Greenhalgh, Halifax, England

[73] Assignee: Zeneca Limited, London, England

[21] Appl. No.: 350,486

[22] Filed: Dec. 7, 1994

Related U.S. Application Data

[63] Continuation of Ser. No. 136,998, Oct. 18, 1993, Pat. No. 5,401,757, which is a continuation of Ser. No. 354,528, May 17, 1989, abandoned, which is a continuation-in-part of Ser. No. 221,895, Jul. 20, 1988, abandoned.

[30] Foreign Application Priority Data

May 20, 1988 [GB] United Kingdom ................ 8811948

[51] Int. Cl.[6] ..................... A01N 37/34; A01N 43/40; A01N 47/30; A01N 55/02
[52] U.S. Cl. ................ 504/149; 514/347; 514/352; 514/367; 514/494; 514/525; 514/596; 514/598; 514/709; 106/15.05
[58] Field of Search ............... 504/330; 514/525, 514/596, 709; 106/15.05

[56] References Cited

U.S. PATENT DOCUMENTS 3,331,735  7/1967  Battershell et al. .............. 167/30
3,632,859  1/1972  Crovetti .............. 260/607 A
3,947,576  3/1976  Kuczkowski et al. .............. 514/347
3,988,294  10/1976  Hill .............. 260/45.8
4,007,258  2/1977  Cohen et al. .............. 424/22
5,125,967  6/1992  Morpeth et al. .............. 424/405

FOREIGN PATENT DOCUMENTS 60-54301  3/1985  Japan .
60-3461   3/1985  Japan .

OTHER PUBLICATIONS

Chemical Abstracts, vol. 100, Nos. 21–22 (1984) p. 274, Abstract No. 179302h.

Primary Examiner—S. Mark Clardy
Attorney, Agent, or Firm—Cushman Darby & Cushman IP Group of Pillsbury Madison & Sutro LLP

[57] ABSTRACT

A composition comprises (a) halogenated aromatic 1,2- or 1,3- dinitrile, (b) a substituted urea and (c) a halogen-containing aromatic alkyl sulphoxide or sulphone. The composition may include other materials for example inorganic diluents such as silica, alumina, titanium, dioxide, zinc oxide, etc. and may also include other anti-microbial agents such are anti-bacterial agents. The composition has anti-microbial properties, particularly anti-fungal and anti-algal properties. The composition can be incorporated into materials such as paint or plastics to provide anti-microbial properties.

14 Claims, No Drawings

SYNERGISTIC FUNGICIDAL COMPOSITION AND USE

This is a continuation of U.S patent application Ser. No. 08/136,998, filed Oct. 18, 1993, now U.S. Pat. No. 5,401,757, which is a continuation of U.S patent application Ser. No. 07/354,528, filed May 19, 1989, now abandoned, which is a continuation-in-part of U.S. patent application Ser. No. 07/221,895, filed Jul. 20, 1988, now abandoned.

The present invention relates to compositions, particularly compositions having anti-microbial properties, and to the use of such compositions as industrial biocides.

Industrial biocides are materials which have antimicrobial activity such as anti-bacterial, anti-fungal and/or anti-algal activity, and hence are useful in the prevention, or reduction, of industrial spoilage due to the activities of a range of microbial species such as bacteria, fungi and/or algae. Materials of this type can be used to protect substrates which are susceptible to the growth of micro-organisms. Thus, depending on its particular properties, an industrial biocide may find application in, for example, the preservation of paints, latices, adhesives, leather, wood, metal working fluids and cooling water.

Many compounds are commercially available which have anti-microbial properties and can be used as industrial biocides. Iodine-containing compounds are available which have anti-fungal properties. Compounds having anti-fungal properties can be incorporated into paints to give improved resistance to the growth of fungi on a film of the paint. However, iodine-containing compounds are generally susceptible to discolouration on exposure to light and hence many iodine-containing compounds are not suitable for use as a paint film fungicide. Furthermore, useful biocides are effective against a wide range of microbial species, and, in particular, activity against a broad spectrum of fungi together with anti-algal properties is desirable. Such characteristics are only rarely attainable in a single material. There have been proposals to use mixtures of biocides but it appears that such mixtures have not been entirely satisfactory. Hence, materials having a useful balance of characteristics are still being sought.

We have now found mixtures of biocides which give a particularly useful balance of properties which is not achieved using other combinations of biocides.

According to the present invention there is provided a composition comprising (a) at least one halogenated aromatic 1,2- or 1,3- dinitrile; (b) at least one substituted urea and (c) at least one halogen-containing aromatic alkyl sulphoxide or sulphone in which when the aromatic group is the only group containing halogen, it contains at least four halogen substituents.

In component (a) the two nitrile groups are positioned in the 1,2- or 1,3- positions relative to each other on the aromatic ring. Thus, component (a) can be a phthalonitrile or an isophthalonitrile. Suitable materials for use as component (a) have the general formula:

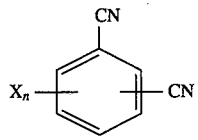

where
  each X, which may be the same or different, is a halogen atom;
  n has a value of from one up to four; and the nitrile groups are either in the 1,2- or 1,3- positions relative to each other.

When the value of n is less than four, the remaining atoms in the aromatic ring are hydrogen atoms. We have obtained useful results when the value of n is four. Each group X is preferably a chlorine or fluorine atom. Conveniently all of the groups X are the same. Compounds which can be used as component (a) of the composition of the present invention are disclosed in U.S. Pat. Nos. 3,290,353 and 3,331,735. As is described in more detail in U.S. Pat. No. 3,290,353, compounds which can be used as component (a) can be prepared by the reaction of the corresponding acid halide, particularly the acid chloride, with ammonia to give the corresponding amide which is then reacted with a dehydrating agent such as phosphorus pentoxide. The foregoing procedure is suitable for the preparation of the chlorinated aromatic dinitrile from which the fluorinated analogue can be prepared by a halogen interchange reaction.

Compounds which can be used as component (a) of the composition of the present invention include tetrachloroisophthalonitrile and tetrafluoroisophthalonitrile.

Compositions having useful properties have been obtained in which component (a) is tetrachloroisophthalonitrile.

Component (b) of the composition of the present invention is at least one substituted urea. The substituted urea typically contains at least one substituent group on each nitrogen atom. One class of urea compound which my be used contains one substituent group which is, or which contains, an aromatic group (an "aromatic substituent") and wherein no other substituent is attached to the nitrogen atom to which the aromatic substituent is attached. One or two substituents may be attached to the other nitrogen and these substituents are typically alkyl, alkenyl, alkynyl, alkoxy, or cycloalkyl groups. Substituted ureas which may be used as component (b) are typically of the general formula:

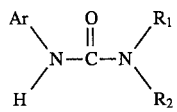

wherein
  Ar is an aryl, substituted aryl, heterocyclic or substituted heterocyclic group;
  $R^1$ is an alkyl, substituted alkyl, alkenyl, substituted alkenyl, alkynyl, substituted alkynyl, cycloalkyl, substituted cycloalkyl, alkoxy or substituted alkoxy group; and
  $R^2$ is a hydrogen atom or a group as defined for $R^1$.

The substituted groups may contain one or more substituents selected from a hydrocarbon group, a halogen atom, a hydrocarbonoxy group, a hydroxy group, and an alkylaminosulphonyl group, or a mixture of such substituents.

The group Ar my be an unsubstituted aryl group such as a phenyl group but my contain at least one substituent which is a halogen atom, an alkyl group, an alkoxy group or an aryloxy group which my itself be substituted. Thus, the group Ar may be, for example, a phenyl, 4-chlorophenyl, 3,4-dichlorophenyl, 4-isopropylphenyl, 3-chloro-4-bromophenyl, 3-chloro-4-methylphenyl, 4(4'-chlorophenoxy)phenyl or 4(4'-methoxyphenoxy)phenyl group. If the group Ar is, or includes, a heterocyclic group, it my be, for example, a benzothiazol-2-yl group or it may be a heterocyclic group having aromatic characteristics such as a pyridyl group.

The groups $R^1$ and $R^2$ are typically unsubstituted. Generally $R^1$ and $R^2$ each contain not more than six carbon atoms, especially not more than four carbon atoms. If $R^2$ is other than a hydrogen atom, the groups $R^1$ and $R^2$ can be the same or different. Typically $R^2$ is a hydrogen atom or a methyl group. The group $R^1$ may be, for example, a methyl, n-butyl, methoxy, 2-methylcyclohexyl, or 3-butynyl group.

It is preferred that the group Ar is unsubstituted or, very preferably, is substituted with one or two substituents which are halogen atoms or lower alkyl groups, that is alkyl groups containing not more than six carbon atoms and especially not more than four carbon atoms. It is especially preferred that, in the compounds containing a preferred group Ar, the groups $R^1$ and $R^2$ are hydrogen, methyl or methoxy and at least one of the groups $R^1$ and $R^2$ is other than hydrogen. Most preferred are the compounds in which $R^1$ and $R^2$ are both methyl groups.

Substituted ureas which can be used as component (b) include 3-(3,4-dichlorophenyl)-1,1-dimethylurea, 3-(3-chloro-4-bromophenyl)-1-methyl-1-methoxyurea, 3-(4-isopropylphenyl)-1,1-dimethylurea, 3-(3,4-dichlorophenyl)-1-methyl-1-methoxyurea, 3-(3-chloro-4-methylphenyl)-1,1-dimethylurea, 1,1-dimethyl-3-phenylurea, 3-(4-chlorophenyl)-1,1-dimethylurea, and 3-(3-chloro-4-methoxyphenyl)-1,1-dimethylurea.

Other substituted ureas include 1,1-dimethyl-3-(3-trifluoromethylphenyl)urea, 3-(3-tertiary butylcarbamoyloxy)-phenyl-1,1-dimethylurea, 1,1-dimethyl-3-(4-trifluoromethylphenyl)urea, 3[3-chloro-4-(chlorodifluoromethylthio)phenyl]-1,1-dimethylurea, 3(3-[(1', 1', 2', 2'-tetrafluoroethoxy]phenyl))-1,1-dimethylurea, 3-(3-chloro-4-trifluoromethoxyphenyl)-1,1-dimethylurea. 3-[4-(4'-chlorophenoxy)phenyl]-1,1-dimethylurea, 3-[4-(4'-methoxyphenoxy)phenyl]-1,1-dimethylurea, 3-(4-chlorophenyl)-1-methyl-1-(3-butynyl)urea, 3-(3,4-dichlorophenyl)-1-methyl-1-n-butylurea, 3-phenyl-1-(2-methylcyclohexyl)urea, and 3-(benzothiazol-2-yl)-1-methylurea.

Compositions having useful properties have been obtained in which component (b) is 3-(3,4-dichlorophenyl)-1,1-dimethylurea.

Substituted ureas which can be used as component (b) can be prepared by known procedures, for example as described in British Patents 691403 and 692589 and U.S. Pat. Nos. 2,655,455 and 2,768,971.

Suitable materials for use as component (c) have the general formula:

$$Ar^1SO_xR^3$$

wherein

Ar$^1$ is an aryl, substituted aryl, heterocyclic or substituted heterocyclic group;

$R^3$ is an alkyl or substituted alkyl, group;

x has a value of one or two; and at least one of the groups Ar$^1$ and $R^3$ contains at least one halogen substituent and Ar$^1$ has at least four halogen substituents if $R^3$ is free of halogen.

The substituents which may be present in the groups Ar$^1$ and $R^3$ include at least one halogen atom, hydrocarbyl group or hydrocarbyloxy group. Ar$^1$ or $R^3$, or both, contain at least one halogen atom substituent.

In one class of compound which can be used as component (c), Ar$^1$ is a heterocyclic group particularly a substituted heterocyclic group having aromatic characteristics such as a pyridine ring which contains at least one halogen substituent, particularly at least two halogen atoms, for example three halogen atoms. In such a compound it is preferred that $R^3$ is an unsubstituted alkyl group containing 1 to 12 carbon atoms and that Ar$^1$ contains st least four halogen substituents. Compounds of this type, and the preparation of such compounds, are described in more detail in British Patent 1103606, and U.S. Pat. Nos. 3,296,272 and 3,371,011. As is described in more detail in the aforementioned patents, compounds of this type can be prepared by the oxidation of the corresponding thiopyridine compound. Suitable compounds of this type include those in which Ar$^1$ is a pyridine ring which contains four halogen substituents, $R^3$ is an unsubstituted lower alkyl group, that is an alkyl group containing up to six carbon atoms and the value of x is two.

Compounds of this type include
2,3,5,6-tetrachloro-4-(methylsulphonyl)pyridine; and
2,3,5,6-tetrachloro-4-(isopropylsulphonyl)pyridine In a further class of compound which can be used as component (c), Ar$^1$ contains an aryl group, $R^3$ is a halogen substituted methyl group and x has a value of two. Compounds of this general type, and the preparation thereof, are described in more detail in U.S. Pat. Nos. 3,632,859 and 3,663,623. As described in U.S. Pat. No. 3,632,859, compounds of this type can be prepared by halogenating a sulphonyl acetic acid, for example using sodium hypoiodite in sodium hydroxide solution. The procedure of U.S. Pat. No. 3,663,623 differs in that the halogensting step is carried out using iodine monochloride in an essentially neutral solution. Suitable compounds of this type include those in which Ar$^1$ is an alkyl substituted aryl group such as a 4-methylphenyl group and $R^3$ is a diiodomethyl group.

Compositions having useful properties have been obtained in which component (c) is 2,3,5,6-tetrachloro-4-(methylsulphonyl)-pyridine or di-iodomethyl-4-methylphenyl sulphone.

As a particular embodiment of the present invention there is provided a composition comprising (a) tetrachloroisophthalonitrile, (b) 3-(3,4-dichlorophenyl)-1,1-dimethylurea and (c) 2,3,5,6-tetra-chloro-4-4-(methylsulphonyl)pyridine or di-iodomethyl-4-methylphenyl sulphone.

The amount of each component in the composition is preferably at least 10% by weight of the total weight of (a), (b) and (c). Typically, the maximum amount of any component is not more than 80% by weight of the total weight of (a), (b) and (c).

It is generally preferred that component (a) is present in an amount of at least 15% by weight of the total weight of (a), (b) and (c). In general it is preferred that the amount of component (a) does not exceed 70% by weight of the total weight of (a), (b) and (c).

Component (b) may be present in an amount of at least 15% by weight of the total weight of (a), (b) and (c). In general it is preferred that the amount of component (b) does not exceed 40% by weight of the total weight of (a), (b) and (c).

Component (c) is generally present in an amount of at least 15% by weight of the total weight of (a), (b) and (c). It is generally preferred that the amount of component (c) does not exceed 50% by weight of the total weight of (a), (b) and (c).

It will be appreciated that the relative amounts of (a), (b) and (c) can be varied and to obtain the optimum properties the amounts used can be varied both in dependence on the specific compounds used as components (a), (b) and (c) and also on the particular system in which the composition is to be used.

In addition to components (a), (b) and (c), the composition may include other, optional, components. These other components may be liquids including water and organic liquids such as aliphatic or aromatic hydrocarbons, halogenated hydrocarbons, ketones, esters, ethers and alcohols. The components of the composition are typically solids and, when used with a liquid, components (a), (b) and (c) are either dissolved or dispersed in the liquid medium. Some of the components of the composition my be more soluble in a particular liquid medium than other solvents and in such a system the composition may be partially dissolved or partially dispersed. However, it is generally preferred to use a liquid medium in which all of components (a), (b) and (c) are dissolved or in which all of components (a), (b) and (c) remain essentially undissolved. If a liquid medium is present, the composition of (a), (b) and (c) may be present in an amount of from 1 up to 99% by weight of the total composition of liquid medium and the composition. Typically, the amount of the composition is from 2 up to 50% by weight of the total of liquid medium and the composition.

The composition may also include other anti-microbial agents, such as, for example, anti-bacterial agents. Compounds which may be incorporated in the composition as anti-bacterial agents include imidazolidinyl urea; 1,2-dibromo-2,4-dicyanobutane; 5-chloro-2-methyl-4-isothiazolin-3-one and the magnesium salts thereof; 2-methyl-4-isothiazolin-3-one; 1,2-benzisothiazolin-3-one and the salts thereof; 2-bromo-2-nitropropane-1,3-diol; gluteraldehyde; poly hexamethylene biguanide; triazine derivatives and oxazolidine and derivatives thereof. A useful effect is obtained when the composition includes 1,2-benzisothiazolin-3-one or a salt thereof.

Alternatively, or additionally, the composition may include one or more solid components, which may act as carriers or diluents. Solid materials which may be used as the optional component include inorganic materials such as metal oxides or mixtures or compounds thereof, for example aluminium oxide, silicon oxide, titanium dioxide, zinc oxide, talc, pyrophyllite, gypsum, kieselguhr, chalk, diatomaceous earth, bentonite and fuller's earth and organic materials such as wheat flour, soybean flour, wood flour, walnut shell flour and lignin. The solid material is preferably in a finely divided form and typically has an average particle size of not more than 5 micrometres. Any optional solid may be added to the composition in an amount of from 1% up to 95% by weight of the total weight of the composition plus optional solid and in general the optional solid will be present in an amount of at least 10% and not more than 80% by weight of the composition.

The composition may include a de-dusting agent, particularly if the composition is in a solid form. Suitable de-dusting agents include dodecyl benzene, tridecyl octadecanoate, trimethylol propane tridodecenoate, twitchel oil, Ensitol USN and mineral oil.

If the composition includes a liquid in which the solid components of the composition are dispersed, the dispersion conveniently contains a surface active agent which is effective as a dispersant to maintain the solid components as a dispersion. Any surface active agent which is effective as a dispersant and is known for use in biocide compositions may be used such as, for example alkylene oxide copolymers, and alkylene oxide adducts of fatty alcohols, alkyl phenols and amines such as ethylene diamine. Other surface active agents which can be used as dispersants include sodium lignosulphonate, EO/PO/EO block copolymers, ethylene oxide condensates with nonyl phenol or beta-naphthol, PO/EO copolymer condensates with nonyl phenol or ethylene diamine and condensates of naphthalene beta-sulphonic acid and formaldehyde. The surfactant is typically present in an amount of from 0.1 to 20% by weight of the weight of the total dispersion in which the surfactant is to be incorporated. The dispersion may include, in addition to the surfactant, other components which are known for inclusion in biocide compositions such as thickening agents. Materials which can be used as thickening agents include polysaccharide xanthan gum, sodium magnesium silicate, heteropolysaccharide, alginates, carboxymethyl cellulose, gum arabic, polyacrylic acid and polyvinyl alcohol.

Components (a), (b) and (c) of the composition of the present invention are generally solid materials. The composition, together with other optional solid materials, may be used as a solid blend, very desirably a powder blend. A solid blend of this type preferably comprises particles having a mean particle size of not more than 25 micrometres and especially not more than 10 micrometres. Components (a), (b) and (c), and other optional solid material, may be available as a powder having a suitable particle size. Any solid the particle size of which is larger than is desirable can be subjected to a suitable particle size reduction stage for example grinding using a pin mill, a ball mill or a laboratory mill obtainable from Christy and Norris. The components of the composition are subjected to a suitable solids blending procedure, for example tumble blending or using a high speed powder mixer such as a Loedige mixer or a Henschel mixer. Preferably any material of large particle size is subjected to a particle size reduction before the solid blending stage is effected. However, it will be appreciated that, if desired, the solids can be blended and the blend obtained then subjected to a particle size reduction step, but this is generally a less satisfactory, less efficient, procedure.

If the composition is mixed with a liquid medium to form a dispersion, mixing with the liquid can be effected using any suitable dispersion technique, for example using a colloid mill, a Silverson or Ultra-Turrax high shear mixer, a bead mill, an attritor mill or a cascade mill. If a high energy dispersion technique is used, this is capable of causing a reduction in the particle size of the solids and hence a preliminary particle size reduction of dry solid may be unnecessary. In preparing a dispersion in a liquid medium, a solid blend may be prepared initially and the blend dispersed in the liquid in the presence of further additives such as surfactants, thickening agents and the like. Alternatively, each solid component of the composition, including any optional solid components, may be dispersed in a liquid medium, which is the same for each solid, and the dispersions obtained are then mixed. A further alternative is to dry blend some of the solid components, form a dispersion of the blend and mix this dispersion with one or more dispersions of other solid components. Such a technique may be useful if one or more solid components have a large particle size which it is necessary to reduce, such a particle size reduction being effected using a high energy dispersion technique and thereafter mixing the resulting dispersion with a dispersion containing the other solid components.

As noted previously herein, the composition of the present invention is a mixture of biocides. Hence, the composition of the present invention can be used as a biocide.

More specifically, the composition of the present invention is especially effective in providing anti-fungal activity. The composition also has useful anti-algol activity. Thus, the composition of the present invention can be used for the treatment of various media to inhibit the growth of microorganisms, particularly fungi and algae.

As a further aspect of the present invention there is provided a method for inhibiting the growth of microorganisms on, or in, a medium which comprises treating the medium with a composition comprising components (a), (b) and (c) as hereinbefore defined.

The composition can be used in conditions in which micro-organisms, especially fungi and algae, grow and cause problems. Systems in which micro-organisms cause problems include liquid, particularly aqueous, systems such as cooling water liquors, metal working fluids, geological drilling lubricants, polymer emulsions and surface coating compositions such as paints, varnishes and lacquers and also solid materials such as wood and leather and synthetic polymers, particularly those containing appreciable proportions of additives. The composition can be included in such materials and is particularly useful when incorporated into a paint, varnish or lacquer to which it provides anti-fungal and anti-algal characteristics. The composition is also useful when incorporated into a synthetic polymer such as polyvinyl chloride which contains a plasticiser such as an ester, for example a diester of phthalic acid or adipic acid, or such as an epoxidised oil.

As a particular aspect of the present invention there is provided a surface coating composition which contains an effective amount of a composition in accordance with the present invention.

The surface coating composition my be a paint, varnish or lacquer and is especially a paint, for example an emulsion paint. The amount of the composition which is present in the surface coating composition is typically in an amount which is sufficient to provide a level of total active ingredients, that is components (a), (b) and (c), which is in the range from 0.001 up to 50% by weight and especially 0.1 up to 2% by weight relative to the total weight of the surface coating composition.

The composition provides anti-fungal and anti-algal properties to the surface coating composition. However, many compounds which are used to provide anti-fungal properties are iodine-containing compounds and, unlike such compounds, the compositions of the present invention show little discolouration of a paint film when exposed to sunlight. Hence, the compositions of the present invention can be used under conditions in which many iodine-containing compounds would give unacceptable discolouration of a paint film whereas the compositions of the present invention cause little, if any, discolouration.

As a further aspect of the present invention there is provided a plasticised polymer composition which contains an effective amount of a composition in accordance with the present invention.

The polymer is typically plasiticised PVC which contains a plasticiser or plasticisers in an amount of from 10% up to 100% by weight relative to the polymer. The composition of the present invention is preferably incorporated into the polymer in an amount of from 0.012 up to 5% of the composition relative to the polymer.

We have found that whilst the compositions of the present invention have particularly useful anti-fungal properties, other compositions containing one or two of components (a), (b) and (c), together with other biocide components, are surprisingly less effective as anti-fungal materials.

Further aspects of the present invention are described in the following illustrative examples. In the following tests and examples, all parts are by weight unless stated to the contrary.

In the following examples, the compositions obtained were subjected to microbiological evaluation as paint film fungicides. The compositions were also tested for anti-algal properties. The microbiological testing was effected as follows:

The products were tested for activity against fungi which were one or more of Alternaria alternata, Aureobasidum pullulans, Cladosporium herbarum, Phoma violacea and Stemphylium dendriticum.

EVALUATION AS A PAINT FILM FUNGICIDE

The compositions to be tested were obtained as described in Examples 1 to 6 and the Comparative Examples. The compositions were added as a solid blend to samples of an exterior acrylic emulsion paint (based on Revacryl 1A latex at pH 9) in glass bottles and mixed to give final active ingredient levels in the paint of 1.0, 0.5 and 0.25% w/v.

The bottles containing paint plus biocide composition were sealed and stored at 40° C. for three days.

Small wooden test pieces were prepared for each paint composition by priming and then brushing on two full even coats.

One set of the coated test pieces was stored at ambient temperature in the dark. A further set of coated test pieces was placed in a leaching device in which the test pieces were sprayed with water for one day and the test pieces were removed from the leaching device and dried. Yet a further set of coated test pieces was subjected to leaching for two days.

The coated test pieces were then transferred to a high humidity chamber. Each test piece was then spray inoculated with a mixed fungal spore suspension of Alternaria alternata, Aureobasidium pullulans, Cladosporium herbarum, Phoma violacea, and Stemphylium dendriticum.

Incubation was carried out at 25° C. for four weeks. After this period the paint films were examined for fungal growth by naked eye and by stereo optical microscope.

EXAMPLES 1 TO 6

A series of compositions in accordance with the present invention, and a series of comparative compositions, were prepared by mixing together, by grinding in a mortar and pestle, two or more solid components in the proportions set out in Table One.

Further details of the compositions formed are given in Table One.

TABLE ONE

| Example or Comp. Example | Component (a) (parts by weight) | | | | | | | | | | |
|---|---|---|---|---|---|---|---|---|---|---|---|
| | NC | DU | ZO | DS | AM | ZPT | BS | PP | TY | DA | TT |
| A | 75 | 25 | | | | | | | | | |
| B | 55 | 25 | 20 | | | | | | | | |
| C | 50 | | | 50 | | | | | | | |
| D | | 20 | | 80 | | | | | | | |
| 1 | 60 | 20 | | 20 | | | | | | | |
| 2 | 40 | 20 | 20 | 20 | | | | | | | |
| 3 | 40 | 20 | | 40 | | | | | | | |
| 4 | 30 | 20 | 20 | 30 | | | | | | | |
| 5 | 55 | 25 | | | 20 | | | | | | |

TABLE ONE-continued

| Example or Comp. Example | Component (a) (parts by weight) | | | | | | | | | | |
|---|---|---|---|---|---|---|---|---|---|---|---|
| | NC | DU | ZO | DS | AM | ZPT | BS | PP | TY | DA | TT |
| 6 | 35 | 25 | 20 | | 20 | | | | | | |
| E | 40 | 20 | | | | | | | | 40 | |
| F | | | 20 | 40 | | | | | | | 40 |
| G | 55 | 25 | | | | 20 | | | | | |
| H | 35 | 25 | 20 | | | 20 | | | | | |
| I | 55 | 25 | | | | | 20 | | | | |
| J | 35 | 25 | 20 | | | | 20 | | | | |
| K | 55 | 25 | | | | | | 20 | | | |
| L | 35 | 25 | 20 | | | | | 20 | | | |
| M | 55 | 25 | | | | | | | 20 | | |
| N | 35 | 25 | 20 | | | | | | 20 | | |

Notes to Table One
(a)
NC is tetrachloroisophthalonitrile.
DU is 3-(3,4-dichlorophenyl)-1,1-dimethylurea.
ZO is zinc oxide having a particle size less than one micrometer.
DS is 2,3,5,6-tetrachloro-4-(methylsulphonyl)pyridine.
AM is di-iodomethyl-4-methylphenylsulphone.
ZPT is zinc 2-mercaptopyridine-N-oxide.
BS is a commercially available biocide which contains 30% by weight of 2-thiocyanomethylthiobenzothiazole as the active ingredient, the remainder being inert solvent.
PP is (RS)-2-(2,4-dichlorophenyl)-1-(1H-1,2,4-triazol-1-yl)hexen-2-ol.
TY is a commercially available biocide which contains 40% by weight of 3-iodo-2-propynyl-N-n-butylcarbamate, as the active ingredient, the remainder being inert.
DA is 3,4,5-trichloro-4-(propylsulphonyl) pyridine.
TT is tetrachloroterephthalonitrile.

EXAMPLES 7 TO 24

The compositions of Examples 1 and 6 and the Comparative Examples were evaluated as paint film fungicides using the technique described previously herein. For comparative purposes paints containing only tetrachloroisophthalonitrile (NC); 3-(3,4-dichlorophenyl)-1,1-dimethylurea (DU); 2,3,5,6-thetrachloro-4-(methylsulphonyl) pyridine (DS); di-iodomethyl-4-methylphenylsulphone (AM); or zinc oxide (ZO) were also evaluated under the same conditions. The results obtained are set out in Table Two.

TABLE TWO

| Example or Comp. Example | Composition | | | Fungal Growth (d) (e) | | |
|---|---|---|---|---|---|---|
| | (a) | (b) | % (c) | UL | L1 | L2 |
| O | A | | 0.25 | 1,1 | 2,2 | 5,5 |
| P | A | | 0.5 | 1,1 | 3,5 | 1,3 |
| Q | A | | 1.0 | 1,1 | 4,4 | 2,3 |
| R | B | | 0.25 | 1,2 | 4,5 | 5,5 |
| S | B | | 0.5 | 2,2 | 3,4 | 2,4 |
| T | B | | 1.0 | 0,2 | 1,2 | 4,5 |
| 7 | 1 | | 0.25 | 0,0 | 2,3 | 5,5 |
| 8 | 1 | | 0.5 | 0,1 | 0,1 | 2,3 |
| 9 | 1 | | 1.0 | 0,0 | 0,0 | 0,0 |
| 10 | 2 | | 0.25 | 0,0 | 1,3 | 5,5 |
| 11 | 2 | | 0.5 | 0,0 | 1,2 | 3,3 |
| 12 | 2 | | 1.0 | 0.0 | 0,0 | 0,0 |
| 13 | 3 | | 0.25 | 0,0 | 1,2 | 1,3 |
| 14 | 3 | | 0.5 | 0,1 | 0,1 | 0,2 |
| 15 | 3 | | 1.0 | 0,0 | 0,0 | 0,0 |
| 16 | 4 | | 0.25 | 0,0 | 0,1 | 3,4 |
| 17 | 4 | | 0.5 | 0,0 | 0,0 | 0,1 |
| 18 | 4 | | 1.0 | 0,0 | 0,0 | 0,0 |
| U | C | | 0.25 | 1,3 | ND | 5,5 |
| V | C | | 0.5 | 1,1 | ND | 1,1 |
| W | C | | 1.0 | 0,1 | ND | 1,1 |
| X | D | | 0.25 | 2,1 | ND | 4,5 |
| Y | D | | 0.5 | 1,1 | ND | 3,3 |
| Z | D | | 1.0 | 0,1 | ND | 0,0 |
| AA | E | | 0.25 | 2,2 | ND | 5,5 |
| AB | E | | 0.5 | 0,0 | ND | 4.3 |
| AC | E | | 1.0 | 0,0 | ND | 5,5 |
| AD | F | | 0.25 | 2,3 | ND | 5,5 |
| AE | F | | 0.5 | 1,3 | ND | 5,5 |
| AF | F | | 1.0 | 1,1 | ND | 4,5 |
| AG | G | | 0.25 | 1,3 | 4.5 | 5,5 |
| AH | G | | 0.5 | 1,1 | 2,2 | 2,3 |
| AI | G | | 1.0 | 0,1 | 1,2 | 0,1 |
| AJ | H | | 0.25 | 0,3 | 5,5 | 3,4 |
| AK | H | | 0.5 | 1,1 | 3,4 | 4,4 |
| AL | H | | 1.0 | 1,1 | 1,2 | 0,0 |
| AMS | I | | 0,25 | 1,2 | 4,5 | 5,5 |
| AN | I | | 0.5 | 0,0 | 4,5 | 5,5 |
| AO | I | | 1.0 | 0,1 | 1,3 | 4,5 |
| AP | J | | 0.25 | 3,5 | 2,5 | 5,5 |
| AQ | J | | 0.5 | 2,3 | 3,5 | 5,5 |
| AR | J | | 1.0 | 0,1 | 2,3 | 5,5 |
| 19 | 5 | | 0.25 | 0,0 | 1,1 | 0,2 |
| 20 | 5 | | 0.5 | 0,0 | 0,0 | 2,2 |
| 21 | 5 | | 1.0 | 0,1 | 0,0 | 0,0 |
| 22 | 6 | | 0.25 | 0,1 | 1,2 | 2,4 |
| 23 | 6 | | 0.5 | 0,0 | 0,1 | 1,2 |
| 24 | 6 | | 1.0 | 0,0 | 0,0 | 0,1 |
| AS | K | | 0,25 | 1,2 | 3,5 | 4,4 |
| AT | K | | 0.5 | 1,1 | 4,5 | 4,4 |
| AU | K | | 1.0 | 0,1 | 4,4 | 2,3 |
| AV | L | | 0.25 | 2,3 | 3,5 | 1,3 |
| AW | L | | 0.5 | 1,3 | 3,5 | 0,1 |
| AX | L | | 1.0 | 0,1 | 2,2 | 1,1 |
| AY | M | | 0.25 | 1,2 | 5,5 | 5,5 |
| AZ | M | | 0.5 | 0,1 | 1,2 | 5,5 |
| BA | M | | 1.0 | 0,0 | 0,1 | 2,2 |
| BB | N | | 0.25 | 5,5 | 5,5 | 5,5 |
| BC | N | | 0.5 | 2,2 | 5,5 | 5,5 |
| BD | N | | 1.0 | 0,0 | 1,1 | 5,5 |
| BE | NC | | 0.25 | 3,4 | 4,4 | 5,5 |
| BF | NC | | 0.5 | 2,3 | 4,5 | 3,5 |
| BG | NC | | 1.0 | 0,0 | 2,5 | 4,5 |
| BH | NIL | | NIL | 5,5 | 5,5 | 5,5 |
| BI | DU | | 1.0 | 5,5 | ND | 5,5 |

TABLE TWO-continued

| Example or Comp. Example | Composition (a) (b) | % (c) | Fungal Growth (d) (e) UL | L1 | L2 |
|---|---|---|---|---|---|
| BJ | DS | 0.25 | 2,2 | ND | 5,4 |
| BK | DS | 0.5 | 1,1 | ND | 2,3 |
| BL | DS | 1.0 | 0,1 | ND | 1,0 |
| BM | AM | 0.25 | 0,0 | ND | 4,4 |
| BN | AM | 0.5 | 0,0 | ND | 1,2 |
| BO | AM | 1.0 | 0,0 | ND | 0,0 |
| BP | ZO | 1.0 | 5,5 | ND | 5,5 |

Notes to Table Two
(a) is as defined in Notes to Table One
(b) Numbers and single letters refer to the products of Examples 1 to 6 and Comparative Examples A to N.
(c) % is given as % w/v of composition addition based on the paint.
(d)
UL means the test piece had not been leached.
L1 means the test piece had been leached for one day.
L2 means the test piece had been leached for two days.
(e)
0 indicates no surface growth.
1 indicates less than 1% fungal growth over surface.
2 indicates 1 to 10% fungal growth over surface.
3 indicates 10 to 30% fungal growth over surface.
4 indicates 30 to 70% fungal growth over surface.
5 indicates greater than 70% fungal growth over surface.

It will be observed that, in comparison to the comparative mixtures, the compositions of the present invention show superior anti-fungal activity both before and after leaching.

EXAMPLES 25 TO 28

Samples of the compositions of Examples 3 to 6 were tested for anti-algal activity. Testing was effected using a shake flask technique over a 21 day test period at an incubation temperature of 21° C. A range of concentrations of the compositions were prepared in an algal growth medium and were challenged with a mixture of two algae, namely Trentepohlia aurea and Nostoc commune. The results of the test are summarised in Table Three.

TABLE THREE

| Example | Composition (b) | MIC (ppm) (f) |
|---|---|---|
| 25 | 3 | 25 |
|  | 4 | 12.5 |
|  | 5 | 12.5 |
|  | 6 | 6.25 |

Notes to Table Three
(b) is as defined in Notes to Table Two.
(f) MIC is the Minimum Inhibitory Concentration of the composition expressed as ppm by weight of the composition relative to the weight of the test medium.

The compositions of the present invention were evaluated as fungicides in PVC film using the following testing procedure:

EVALUATION AS FUNGICIDE IN PVC FILM

The compositions to be tested were obtained as described in Examples 3 and 4. PVC pellets were placed in a kitchen mixer bowl and a composition obtained as described in Example 3 or Example 4 was added and the contents of the bowl were then mixed for two minutes without heating. The bowl was then heated with steam and the other components of the PVC formation were then added slowly, the other components, and the proportions thereof being as set out in the following "PVC Formulations Table". The resulting blend was mixed until the sample became a fluffy dry powder.

PVC Formulation Table

| Component | Formulation (phr) | | | | | | | |
|---|---|---|---|---|---|---|---|---|
|  | A | B | C | D | E | F | G | H |
| PVC | 100 | 100 | 100 | 100 | 100 | 100 | 100 | 100 |
| DOP | 50 | 60 | 50 | 60 |  |  |  |  |
| ESO | 7 | 10 | 7 | 10 | 7 | 10 | 7 | 10 |
| Phos | 2 | 2 |  |  | 1 | 1 |  |  |
| BaZn | 2 | 2 |  |  | 2 | 2 |  |  |
| SA | 0.5 | 0.5 | 0.5 | 0.5 | 0.5 | 0.5 | 0.5 | 0.5 |
| CaZn |  |  | 2 | 2 |  |  | 2 | 2 |
| 1178 |  |  | 0.5 | 0.5 |  |  | 0.5 | 0.5 |
| DOA |  |  |  |  | 50 | 60 | 50 | 60 |

Notes to PVC formulations table
PVC is a polymer available from Georgia Gulf Corp, of Plaquemine, LA, USA, as PVC-2095 resin.
DOP is bis(2-ethylhexyl)phthalate
ESO is epoxidised soybean oil.
Phos is an alkyl aryl phosphite obtainable from the Argus Division of Witco Corp, Brooklyn, NY, USA as LE98.
BaZn is a barium - zinc stabiliser obtainable from the Argus Division of Witco as LZ11.
SA is octadecanoic acid.
CaZn is a calcium - zinc stabiliser obtainable from the Argus Division of Witco as LN138.
1178 is an additive obtainable from the Argus Division of Witco as Mark 1178.
DOA is bis(2-ethylhexyl)adipate.

Each of the PVC formulations was formed into film using a three-quarter inch (19 mm) Brabender Extruder having a 4 inch (10.2 cm) wide die gap of variable thickness. The extruder was operated at 40 r.p.m. with a temperature profile of 155° C., 170° C. and 190° C. The extruded polymer was passed onto a chill roll operating at 9 r.p.m. The film obtained had a thickness of 8–12 micrometres. The film was cut into 1.5 inch (3.81 cm) squares which were placed flat on a pre-poured basal salts medium containing 2% noble agar. The basal salts medium contained 2 $g/dm^3$ ammonium sulphate; 4 $g/dm^3$ potassium dihydrogen phosphate; 4 $g/dm^3$ sodium hydrogen phosphate; 0.2 $g/dm^3$ magnesium sulphate heptahydrate; 0.001 $g/dm^3$ calcium chloride dihydrate and 0.002 $g/dm^3$ ferrous sulphate heptahydrate, the pH of the mixture having been adjusted to 5.5 by the addition of Normal hydrochloric acid.

The fungi used in the tests were separately grown in a series of basal salts media containing 2% noble agar and larger proportions (10% in the final medium) of a plasticiser which was either bis(2-ethylhexyl)phthalate; bis(2-ethylhexyl)adipate or epoxidised soybean oil. The cultures were incubated at 30° C. and 96% humidity.

The dishes containing the film were incubated for 7–10 days at 30° C. and 96% humidity and then inspected for fungal growth.

EXAMPLES 29 TO 52

The compositions of Examples 3 and 4 were evaluated as fungicides in PVC film using the technique described previously herein. For comparative purposes a PVC film which contained no added fungicide was evaluated under the same conditions. In each test a single fungus was used. The results obtained are set out in Table four.

TABLE FOUR

| Example or Comp. Ex. | Composition (b) | % (h) | PVC (i) | Fungal Growth (j) AN | PC |
|---|---|---|---|---|---|
| BQ | NIL | NIL | A | a/b | f |
| BR | NIL | NIL | B | c | f |
| BS | NIL | NIL | C | a | e |
| BT | NIL | NIL | D | 0 | f |
| BU | NIL | NIL | E | 0 | e |
| BV | NIL | NIL | F | 0 | e |
| BW | NIL | NIL | G | a | f |
| BX | NIL | NIL | H | 0 | e |
| 29 | 3 | 0.5 | A | 0 | 0 |
| 30 | 3 | 0.5 | B | 0 | 0 |
| 31 | 3 | 0.5 | C | 0 | 0 |
| 32 | 3 | 0.5 | D | 0 | 0 |
| 33 | 3 | 0.5 | E | 0 | 0 |
| 34 | 3 | 0.5 | F | 0 | 0 |
| 35 | 3 | 0.5 | G | 0 | 0 |
| 36 | 3 | 0.5 | H | 0 | 0 |
| 37 | 3 | 0.15 | A | 0 | 0 |
| 38 | 3 | 0.15 | B | 0 | 0 |
| 39 | 3 | 0.15 | C | 0 | 0 |
| 40 | 3 | 0.15 | D | 0 | 0 |
| 41 | 3 | 0.15 | E | 0 | 0 |
| 42 | 3 | 0.15 | F | 0 | 0 |
| 43 | 3 | 0.15 | G | 0 | 0 |

| Example or Comp. Ex. | Composition (b) | % (h) | PVC type (i) | Fungal Growth (j) AN | PC |
|---|---|---|---|---|---|
| 44 | 3 | 0.15 | H | 0 | 0 |
| 45 | 4 | 0.15 | A | 0 | 0 |
| 46 | 4 | 0.15 | B | 0 | 0 |
| 47 | 4 | 0.15 | C | 0 | 0 |
| 48 | 4 | 0.15 | D | 0 | 0 |
| 49 | 4 | 0.15 | E | 0 | 0 |
| 50 | 4 | 0.15 | F | 0 | 0 |
| 51 | 4 | 0.15 | G | 0 | 0 |
| 52 | 4 | 0.15 | H | 0 | 0 |

Notes to Table Four
(b) is as defined in Notes to Table Two.
(h) % is given as % w/w of composition based on the PVC content of the formulation.
(i) A to H are the formulations as set out in the PVC Formulations Table.
(j)
AN is Aspergillus niger
PC is Penicillium citrenum
0 indicates no growth was observed
a indicates very slight growth was observed
b indicates small clusters were observed
c indicates large clusters were observed
d indicated growth along three edges was observed
e indicates growth along all edges was observed
f indicates the film surface was fully covered In the foregoing tests, the films were opaque. However, films containing the compositions in an amount of 0.75%, 1.0% or 2.0%, were translucent.

We claim:

1. A composition comprising (a) at least one halogenated aromatic 1,2- or 1,3-dinitrile, (b) at least one substituted urea, and (c) at least one compound of formula $$Ar^1SO_xR^3$$

wherein
$Ar^1$ is aryl or alkyl substituted aryl;
$R^3$ is alkyl containing at least one halogen substituent; and
x is 1 or 2.

2. The composition of claim 1 wherein the dinitrile is of the formula:

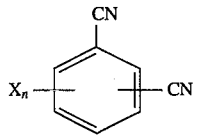

where
each X, which may be the same or different, is a halogen atom;
n has a value of from one up to four; and
the nitrile groups are either in the 1,2- or 1,3- positions relative to each other.

3. The composition of claim 1 wherein the substituted urea is of the formula:

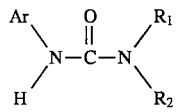

wherein
Ar is an aryl, substituted aryl, heteroaryl, substituted heteroaryl, heterocyclic or substituted heterocyclic group;
$R^1$ is an alkyl, substituted alkyl, alkenyl, substituted alkenyl, alkynyl, substituted alkynyl, cycloalkyl, substituted cycloalkyl, alkoxy or substituted alkoxy group; and
$R^2$ is a hydrogen atom or a group as defined for $R^1$.

4. The composition of claim 3 wherein the group Ar is or contains one or two substituents which are halogen atoms or lower alkyl groups.

5. The composition of claim 4 wherein $R^1$ and $R^2$ are hydrogen, methyl or methoxy and at least one of the groups $R^1$ and $R^2$ is other than hydrogen.

6. The composition of claim 1 wherein $R^3$ is a hydrogen substituted methyl group and x has a value of two.

7. The composition of claim 1 wherein (a) is tetrachloroisophthalonitrile; (b) is 3-(3,4-dichlorophenyl)-1,1-dimethylurea and (c) is di-iodomethyl-4-methylphenyl sulphone.

8. The composition of claim 1 which contains at least 10% by weight of the total weight of (a), (b) and (c) of each of (a), (b) and (c).

9. The composition of claim 1 which includes at least one further component which is a further solid component which is at least one of aluminium oxide, silicon oxide, titanium dioxide, zinc oxide, talc, pyrophyllite, gypsum, kieselguhr, chalk, diatomaceous earth, bentonite, fuller's earth, wheat flour, soybean flour, wood flour, walnut shell flour or lignin.

10. A composition according to claim 1 comprising:
(a) 30 to 60% by weight of tetrachloroisophthalonitrile;
(b) 20 to 25% by weight of 3-(3,4-dichlorophenyl)-1,1-dimethylurea; (c) 20 to 40% by weight of a halogen containing aromatic alkyl sulphone which is di-iodomethyl-4-methylphenyl sulphone; and (d) 0 to 20% by weight of at least one solid component selected from the group consisting of aluminum oxide, silicon oxide, titanium dioxide, zinc oxide, talc, pyrophyllite, gypsum, kieselguhr, chalk, diatomaceous earth, bentonite, fuller's earth, wheat flour, soybean flour, wood flour, walnut shell flour and lignin.

11. A composition comprising:
(a) between 15% and 70% by weight of a tetrahalogenated aromatic 1,2- or 1,3-dinitrile;

(b) between 15% and 40% by weight of a substituted urea of the formula:

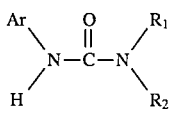

wherein

Ar is a unsubstituted aryl group or is an aryl group substituted with one of two substituents which are halogen atoms or $C_1$–$C_6$ alkyl groups;

$R^1$ is methyl or methoxy; and $R^2$ is hydrogen, methyl or methoxy; and (c) between 15% and 50% by weight of at least one compound of the formula $$Ar^1SO_xR^3$$

wherein $Ar^1$ is aryl or alkyl substituted aryl;

$R^3$ is an alkyl which contains at least one halogen substituent; and x has a value of one or two; wherein the weight percents are based upon the total weight of (a), (b) and (c).

12. The composition of claim 11 wherein (a) is tetrachloroisophthalonitrile or tetrafluoroisophthalonitrile; (b) is 3-(3, 4-dichlorophenyl)-1,1-dimethylurea, 3-(3-chloro-4-bromophenyl -1-methyl-1-methoxyurea, 3-(4-isopropylphenyl)-1,1-dimethylurea, 3-(3,4-dichlorophenyl)-1-methyl-1-methoxyurea, 3-(3-chloro -4-methylphenyl)-1, 1-dimethylurea, 1,1-dimethyl-3-phenylurea, 3-(4-chlorophenyl)-1,1-dimethylurea or 3-(3-chloro-4-methoxyphenyl) -1,1-dimethylurea; and (c) is di-iodomethyl-4-methylphenyl sulphone.

13. The composition of claim 11 wherein (a) is tetrachloroisophthalonitrile; (b) is 3-(3,4-dichlorophenyl)-1,1-dimethylurea and (c) is di-iodomethyl-4-methylphenyl sulphone.

14. A method for inhibiting the growth of micro-organisms on, or in, a medium which comprises treating the medium with the composition of claim 1.

* * * * *